United States Patent [19]

Narayanan et al.

[11] Patent Number: 4,997,952

[45] Date of Patent: Mar. 5, 1991

[54] N-PYRROLIDONYL METHYLTRIPHENYL PHOSPHONIUM SALTS AND METHOD FOR THEIR PREPARATION AND USE

[75] Inventors: Kolazi S. Narayanan, Palisades Park; Paul D. Taylor, West Milford, both of N.J.

[73] Assignee: GAF Chemicals Corporation, Wayne, N.J.

[21] Appl. No.: 420,767

[22] Filed: Oct. 12, 1989

[51] Int. Cl.$^5$ .......................... C07F 9/54; C07B 43/00; C07D 207/267; C07D 207/27
[52] U.S. Cl. .................................. 548/413; 548/543; 548/544; 548/545
[58] Field of Search .......................................... 548/413

[56] References Cited

U.S. PATENT DOCUMENTS 4,128,558 12/1978 Hendricks ........................... 548/413

Primary Examiner—Mark L. Berch

Attorney, Agent, or Firm—McAulay Fisher Nissen & Goldberg

[57] ABSTRACT

A novel triphenylphosphonium salts of chloromethyl pyrrolidone having the formula:

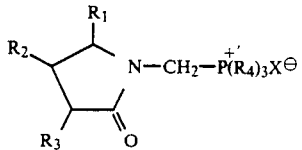

wherein $R_1$, $R_2$, and $R_3$ may be the same or different and may be hydrogen, lower alkyl, lower alkoxy, lower alkenyl, lower cycloalkyl, and lower carboalkoxy, phenyl, substituted phenyl, naphthyl, and substituted naphthyl, $R_4$ is lower alkyl or phenyl and X is an anion. The compounds are useful in Wittig-type reactions and as phase transfer catalysts. A method for preparing the inventive compound is also disclosed.

5 Claims, No Drawings

N-PYRROLIDONYL METHYLTRIPHENYL PHOSPHONIUM SALTS AND METHOD FOR THEIR PREPARATION AND USE

BACKGROUND OF THE INVENTION

1. Field of the Invention

The invention relates to a new phosphonium salt having applications in organic synthesis as a reagent in Wittig-type reactions and as a phase transfer catalyst. More particularly, the present invention provides a novel N-pyrrolidonyl methyltriorganophosphonium salt and a method for preparation thereof.

2. Background of the Invention

It is known that the 2-pyrrolidonyl moiety by itself or in substituted form, has the tendency of endowing numerous organic compounds with improved water solubility and increased biodegradability. 2-Pyrrolidone itself is water soluble and biodegradable as is polyvinylpyrrolidone, even when it is of a high molecular weight. The pyrrolidonyl and substituted pyrrolidonyl moiety have been utilized as a substituent for many organic acids, organic bases, and neutral compounds in order to increase the water solubility and biodegradability of the parent molecule. However, synthesis of compounds having such groups present difficulty in terms of attaching the group to a particular molecule whose solubility or biodegradability it is desired to enhance.

Triphenylphosphonium salts have been known to be useful reagents for participation in the Wittig reaction. In this reaction, a carbonyl oxygen atom can be replaced by a methylene group. (See Advanced Organic Chemistry, Fieser & Fieser, Rineholt Publishing Corp., 1961, p. 482–483 and see Fieser & Fieser, "Reagents for Organic Synthesis," vol. 6, Wiley Interscience (1977), pages 404–406; 640–641.) However, the preparation of appropriate phosphonium salts for use in the Wittig reaction represent significant advances in synthetic organic chemistry. (See Organic Reactions, Ed. Roger Adams, et al, vol. 14, Wiley (1965), ch. 3.)

Also, quaternary ammonium and phosphonium salts have been used as phase transfer catalysts. Such catalysts are utilized when a chemical reaction is carried out wherein the two reactants are present in different phases. The phase transfer catalyst orients itself at the interface of the two phases and aids the reaction via equilibrium reactions involving phase transfer. New and/or improved phase transfer catalysts are always desirable, particularly if they can be produced economically. (See Fieser & Fieser, "Reagents for Organic Synthesis," vol. 6, Wiley Interscience (1977), pages 404–406; 640–641.)

A problem which also is presented to the synthetic organic chemist is that known phosphonium salts are incapable of adding a pyrrolidonyl moiety to organic ketones or aldehydes. Consequently, the enhanced properties resulting from such an addition cannot be achieved.

SUMMARY OF THE INVENTION

We have discovered a novel triphenylphosphonium salt of chloromethyl pyrrolidone which can be utilized in the Wittig-type reaction to produce ethylenic compounds which contain a pyrrolidone moiety. As a result, the inventive phosphonium salt can be utilized to introduce this very useful pyrrolidone moiety into a large variety of compounds, including polymers, to produce enhanced water solubility and biodegradability.

More particularly, the compounds of the present invention have the formula

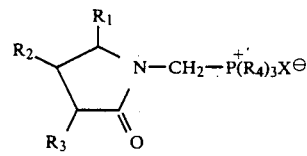

wherein $R_1$, $R_2$, and $R_3$ may be the same or different and may be hydrogen, lower alkyl, lower alkoxy, lower alkenyl, lower cycloalkyl, and lower carboalkoxy, phenyl, substituted phenyl, naphthyl, and substituted naphthyl, $R_4$ is lower alkyl or phenyl and X is an anion.

The inventive compounds are prepared by reacting

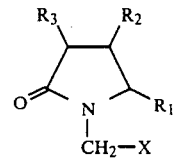

wherein X is $Cl^{31}$, $Br^{31}$, $I^{31}$, $HSO_4^{31}$, $PF_6^{31}$, or $H_2PO_4^{31}$, or other suitable leaving group with a trialkyl or triphenyl phosphine wherein the alkyl portion of the phosphine is lower alkyl.

DESCRIPTION OF THE PREFERRED EMBODIMENT

In formula I, the prefix "lower" in connection with alkyl, cycloalkyl, alkenyl, alkoxy, esters, and like moieties means having from 1 to 12 carbon atoms. The word "substituted" in connection with aromatic groups means that the groups may be substituted with the conventional substituents, such as, alkyl, alkoxy, chloride, nitro, cyano, and the like.

Preferably, $R_1$, $R_2$, and $R_3$ are hydrogen, or straight or branched chain alkyl groups having up to 4 carbon atoms.

The compounds of the present invention are generally solids, but can be liquids or oils. They are generally soluble in polar solvents, such as, water, methanol, N-methyl-pyrrolidone, dimethylformamide, and dimethylsulfoxide. They are insoluble in ether and sparingly soluble in toluene and acetone.

Particularly preferred is a compound wherein x is chloride and $R_1$, $R_2$, and $R_3$ are hydrogen.

The compound of the present invention is preferably synthesized by reacting a substituted or unsubstituted N-2-pyrrolidonylmethyl halide with triphenylphosphine according to the following reaction sequence:

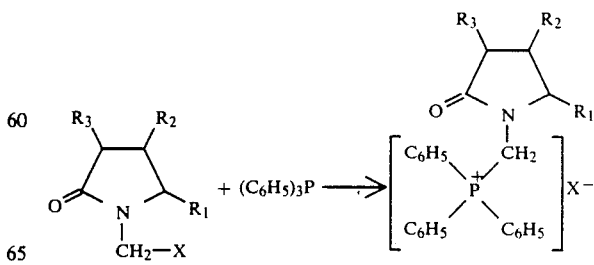

The molar ratios of the reactants may be chosen so as to produce the desired result. Generally, the reaction of the triorganophosphine to the N-2-pyrrolidonylmethyl halide is 1:1. The reaction may be carried out either by merely mixing the reactants in a neat form or in an inert solvent. The temperature used for the reaction may be ambient or elevated temperatures. Preferably, the reaction may be carried out at temperatures from about 25-140° C. and most preferably is carried out at the reflux temperature of the solvent.

The amount of solvent used is not critical so long as the product is insoluble in the solvent so that it will precipitate from the reaction mixture. Preferably, the amount of solvent is from about 2 to 8 times the weight of the reactants and will also depend on the relative solubilities. Most preferably, the amount of solvent is about 3 times the total weight of the reactants.

Generally, the reaction is carried out between ambient and reflux temperature, depending on the reflux temperature of the solvent. Also, the period of the reaction depends on the temperature used and may vary from 1 to about 24 hours.

The progress of the reaction can be easily monitored from nmr and IR measurements of samples of the reaction mixture. Thus, triphenyl phosphine signals (31 Pnmr) appear about 5 ppm upfield from 85% $H_3PO_4$, whereas the phosphonium salts generally appear around 20 ppm downfield from 85% $H_3PO_4$. The reaction time is monitored for the near or total disappearance of the upfield triphenyl phosphine signal and the total presence of the phosphonium salt downfield signal. The reaction may be carried out under an inert atmosphere, e.g., nitrogen, argon, and the like, so as to prevent oxidation by oxygen in the air. The product precipitates from the reaction mixture and is separated therefrom. It is best to collect the product under an inert atmosphere.

The compound of the present invention is suitable for carrying out the Wittig reaction in order to produce a compound having the 2-pyrrolidonyl moiety. Typically, the reaction is carried out by reacting the inventive phosphonium salt with a carbonyl compound in the presence of a strong base as a catalyst. Generally, the Wittig reaction is carried out at a temperature from about −78 to 120° C. in an inert atmosphere (nitrogen or argon) depending upon the reactivity of the carbonyl compound and the stability of the ylid which is the intermediate produced from the phosphonium salt according to the following reaction sequence:

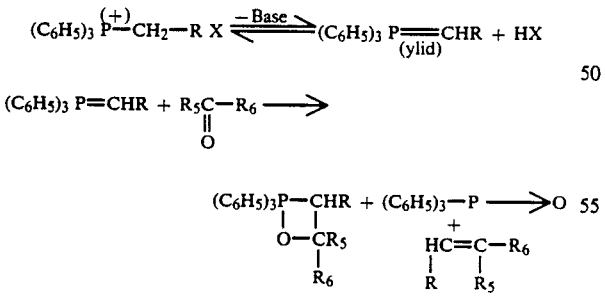

$R_5$ and $R_6$ may be hydrogen, lower alkyl, lower alkenyl, lower cycloalkyl, phenyl, substituted phenyl, naphthyl, and substituted naphthyl, with the proviso that $R_5$ and $R_6$ may not be hydrogen at the same time.

The standard procedure for carrying out the Wittig reaction is to use a 20-30% solution of the phosphonium salt in a solvent, such as, dimethylformamide. A stoichiometric amount of a strong base, such as, $NaOC_2H_5$, $NaOCH_3$, NaH is added to a cooled solution of the phosphonium salt while under an inert atmosphere. A solution of the carbonyl compound is added to the thus obtained solution in the same solvent. After admixing the reagents, the contents are warmed gradually to the desired reaction temperature. A conventional workup procedure is utilized. The reaction products are poured into acidified water after completion of the reaction, the olefin is extracted in a solvent, e.g., ether; it is washed, the solvent is removed, and purification is carried out by distillation or crystallization.

Of course, various carbonyl-containing compounds may be utilized to produce the ultimate products containing the pyrrolidone moiety.

Compounds in accordance with the present invention are also suitable for use as phase transfer catalysts. Such catalysts are generally compounds which contain polar and nonpolar regions in the same molecule. Typical reactions in which a compound of the present invention may be utilized as a phase transfer catalyst are shown in the following two reaction sequences:

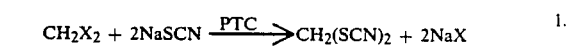

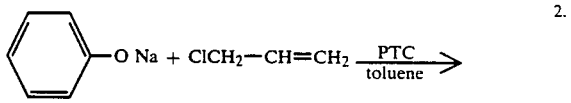

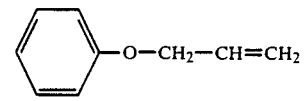

wherein:
X is halide, and
PTC is a phase transfer catalyst, e.g.

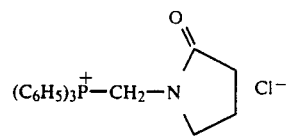

The present compounds are advantageous because of the presence of the phenyl groups as the non-polar portion and the pyrrolidone moiety as the polar region in the molecule apart from the charged region of the central phosphorous atom and the anion. The ligands on the phosphorous atom form polar and nonpolar regions and therefore would distribute over a larger region of the interface between the two phases of the reactants.

The reaction sequence in a Wittig reaction would be as shown below:

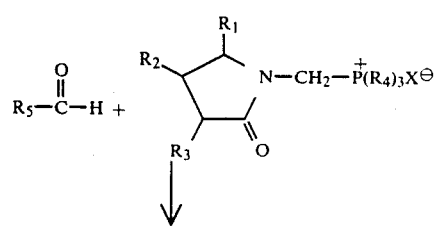

-continued

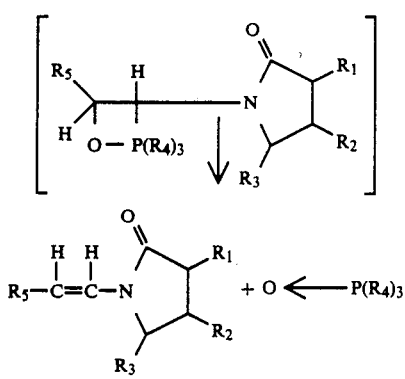

wherein $R_1$, $R_2$, $R_3$, $R_4$, $R_5$ and X have the meanings indicated previously.

For example, $R_5$ could be a phenyl group in which case the reactant would be benzaldehyde. Numerous others can be utilized.

The following example illustrates the present invention:

Synthesis of N-pyrrolidonylmethyl Triphenyl Phosphonium Chloride

A 100 ml round bottom flask, fitted with a magnetic stirrer, water condenser, dropping funnel, thermometer, nitrogen gas inlet and outlet, was prepared. The flask was charged with 13.1 grams of triphenylphosphine (0.05 mole) dissolved in 50 ml of toluene. A solution of 6.6 grams of N-chloromethyl pyrrolidone (N-2-pyrrolidonylmethyl chloride) (0.05 mole) dissolved in 20 ml of toluene was dropped into the flask over a period of approximately 10 minutes, with stirring of the flask contents. The solution turned cloudy as soon as addition of the N-chloromethyl pyrrolidone solution was initiated. After the addition, the mixture was allowed to stand at room temperature for 1 hour with stirring.

The reaction was completed by heating under reflux for 22 hours. Cooling produced a solid product (N-pyrrolidonyl methyl triphenyl phosphonium chloride) which was separated by filtration. The filtered material was washed with toluene, followed by ether, and dried in a vacuum and stored under nitrogen. The amount of filtered material weighed 19.0 grams which represents essentially a quantitative yield. It was stored in suspension in anhydrous ether in a refrigerator to avoid any moisture absorption and air oxidation.

The product obtained was insoluble in ether, sparingly soluble in toluene, slightly soluble in chloroform and methylene dichloride, and soluble in water MeOH, DMSO, DMF, NMP. The infrared, Hnmr, $^{31}$Pnmr spectra, and elemental analysis were consistent with the structural formula:

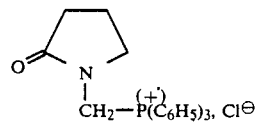

The title compound itself showed the following characteristics:

IR: cm$^{31}$·3054, 1587, 1455 (aromatic) 1692 C-O; 1438 P(C$_6$H$_5$);

Hnmr ppm from TMS (CDcl$_3$):
7.5-8.2, aromatic, multiplet; 15 H:
6.03-6.16, CH$_2$ α to P, doublet, 2H,
3.5-3.6, CH$_2$ α to N, multiplet, 2H,
2.08-2.24, CH$_2$ α to C=0, multiplet, 2H,
1.79-1.98, CH$_2$ β to C=0, multiplet, 2H.

31 Pnmr One signal centered at −19 ppm, downfield from 95% H$_3$PO$_4$.

| | Elemental Analysis: | |
| --- | --- | --- |
| | Calculated | Found |
| % C | 67.07% | 67.15% |
| H | 5.59% | 5.98% |
| N | 3.40% | 3.29% |
| Cl | 8.63% | 8.92% |

The purified product after filtering and washing with ether melted at 176-180°C. with decomposition.

What is claimed is:

1. A compound having the formula

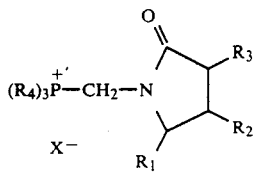

wherein $R_1$, $R_2$, and $R_3$ may be the selected from the group consisting of hydrogen, lower alkyl, lower alkoxy, lower alkenyl, lower cycloalkyl, and lower carboalkoxy, phenyl, substituted phenyl, naphthyl, and substituted naphthyl;
$R_4$ is lower alkyl or phenyl; and
X is an anion.

2. The compound of claim 1 wherein X is Cl$^{31}$, Br$^{31}$, I$^{31}$, HSO$_4$$^{31}$, H$_2$PO$_4$$^{31}$ or PF$_6$$^{31}$.
3. The compound of claim 1 wherein $R_4$ is phenyl.
4. The compound of claim 1 wherein X is chloride.
5. A compound having the formula

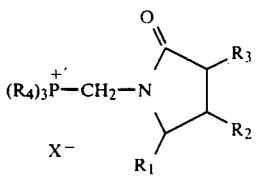

wherein
$R_1$, $R_2$, and $R_3$ are hydrogen;
$R_4$ is lower alkyl or phenyl; and
X is an anion.

* * * * *